(12) United States Patent
Kacker et al.

(10) Patent No.: US 11,490,988 B2
(45) Date of Patent: Nov. 8, 2022

(54) FACE-MOUNTED, NEGATIVE-PRESSURE ANTECHAMBER

(71) Applicant: CORNELL UNIVERSITY, Ithaca, NY (US)

(72) Inventors: Ashutosh Kacker, New York, NY (US); Mark Lee, New York, NY (US); Theodore Schwartz, New York, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 17/065,218

(22) Filed: Oct. 7, 2020

(65) Prior Publication Data
US 2021/0346118 A1 Nov. 11, 2021

Related U.S. Application Data

(60) Provisional application No. 63/021,722, filed on May 8, 2020.

(51) Int. Cl.
*A61B 90/40* (2016.01)
*A41D 13/11* (2006.01)
(Continued)

(52) U.S. Cl.
CPC .............. *A61B 90/40* (2016.02); *A41D 13/11* (2013.01); *A62B 18/02* (2013.01); *A62B 23/02* (2013.01);
(Continued)

(58) Field of Classification Search
CPC .............. A61M 1/0088; A61M 1/0031; A61M 1/0039; A61M 1/064; A61M 5/422;
(Continued)

(56) References Cited

U.S. PATENT DOCUMENTS 2,612,892 A * 10/1952 Beatman ................ A61H 9/005
601/160
2,927,577 A * 3/1957 Nicolaie ................ A61H 9/005
601/6

(Continued)

OTHER PUBLICATIONS

Chari et al., "Aeorosol Dispersion During Mastoidectomy and Custom Mitigation Strategies for Otologic Surgery in the COVID-19 Era," American Academy of Otolaryngology—Head and Neck Surgery, pp. 1-7, 2020.

(Continued)

*Primary Examiner* — Ophelia A Hawthorne
(74) *Attorney, Agent, or Firm* — Norton Rose Fulbright US LLP

(57) ABSTRACT

Embodiments described herein provide systems and methods for protecting doctors and others from pathogenic microorganisms aerosolized during surgical and other procedures on patients. The systems and methods generally operate by forming a partially-enclosed chamber around the patient's face during the procedure. A facial adapter and facial shield isolate a portion of the patient's face from the surrounding environment. The partially-enclosed chamber is connected to a vacuum source that brings the pathogenic particles through a filter, which further decreases the number of pathogenic particles expelled into the environment.

19 Claims, 15 Drawing Sheets

(51) Int. Cl.
  *A62B 18/02* (2006.01)
  *A62B 23/02* (2006.01)
  *B33Y 80/00* (2015.01)
  *A61B 17/24* (2006.01)
  *A61C 7/00* (2006.01)
  *A61F 9/007* (2006.01)

(52) U.S. Cl.
  CPC ......... *A61B 17/24* (2013.01); *A61B 2090/401* (2016.02); *A61C 7/00* (2013.01); *A61F 9/007* (2013.01); *B33Y 80/00* (2014.12)

(58) Field of Classification Search
  CPC .......... A61M 16/0497; A61M 16/0434; A61M 16/0488; A61H 15/0092; A61H 7/003; A61H 2201/0157; A61H 2205/022; A61H 2201/013; A61H 9/005; A61H 9/0057; A61H 9/0071; A61H 7/008; A61H 2201/0153; A61H 2201/1238; A61H 9/00; A61H 2201/1604; A61H 2035/004; A61H 2201/1635; A61H 2209/00; A61B 90/40; A61B 17/24; A62B 18/02; A62B 23/02; B33Y 80/00; A61C 5/90; A61C 17/08; A61C 17/0208; A61C 19/066; A61C 5/82; A61C 7/36; A61C 7/08; A61C 5/80; A41D 13/11
  See application file for complete search history.

(56) References Cited

U.S. PATENT DOCUMENTS

| | | | | |
|---|---|---|---|---|
| 3,794,035 A * | 2/1974 | Brenner | ............... | A61H 9/005 604/315 |
| 4,326,515 A * | 4/1982 | Shaffer | ............. | A61M 16/0488 128/207.17 |
| 4,834,110 A * | 5/1989 | Richard | ............... | A61B 5/4277 600/573 |
| 4,989,596 A * | 2/1991 | Macris | .................. | A61M 16/06 128/201.28 |
| 5,676,133 A * | 10/1997 | Hickle | .................. | A61M 16/00 128/202.27 |
| 6,561,190 B1 * | 5/2003 | Kwok | ................... | A61M 16/06 128/205.24 |
| 2003/0024533 A1 | 2/2003 | Sniadach | | |
| 2005/0187502 A1 * | 8/2005 | Krempel | .................. | A61F 7/02 602/5 |
| 2008/0053449 A1 | 3/2008 | Lindblom et al. | | |
| 2008/0078896 A1 * | 4/2008 | Browne | ................ | F16B 1/0014 248/205.8 |
| 2010/0122705 A1 * | 5/2010 | Moenning, Jr. | ..... | A61M 16/104 128/206.24 |
| 2013/0172768 A1 | 7/2013 | Lehman | | |
| 2017/0173371 A1 * | 6/2017 | Truex | ................... | B29C 64/393 |

OTHER PUBLICATIONS

Chen et al., "Demonstration and Mitigation of Aerosol and Particle Dispersion during Mastoidectomy Relevant to the COVID-19 Era," published by Wolters Kluwer Health, Inc. on behalf of Otology & Neurotology, Inc., 41:1230-1239, 2020.
Workman et al., "Airborne Aerosol Generation During Endonasal Procedures in the Era of COVID-19: Risks and Recommendations," Otolaryngology—Head and Neck Surgery, pp. 1-21, 2020.
Workman et al., "Endonasal Instrumentation and Aerosolization Risk in the Era of COVID-19: Simulation, Literature Review, and Proposed Mitigation Strategies," International Forum of Allergy & Rhinology, vol. 10, No. 7, pp. 798-805, Jul. 2020.
Workman et al., "Suction Mitigation of Airborne Particulate Generated During Sinonasal Drilling and Cautery," doi.org/10.1111/alr.22644, pp. 1-14, 2020.
International Search Report dated Aug. 6, 2021 for PCT/US2021/031377, International Filing Date May 7, 2021, 2 pages.

* cited by examiner

FACE-MOUNTED, NEGATIVE-PRESSURE ANTECHAMBER

CROSS-REFERENCE

The present application claims priority to U.S. Provisional Patent Application No. 63/021,722, entitled "face-mounted, negative-pressure antechamber invention for endoscopic procedures," filed May 8, 2020, which application is entirely incorporated herein by reference for all purposes.

TECHNICAL FIELD

The present disclosure relates generally to systems and methods for protecting doctors and others from pathogenic microorganisms exhaled by patients undergoing surgical and other procedures.

BACKGROUND

Since the first cases of COVID-19 infection from the SARS-CoV-2 virus in December 2019, healthcare systems around the world have undergone dramatic organizational changes. In just a few months, the novel coronavirus took hold in all parts of the globe accompanied by exponential growth in new cases, hospitalizations, and mortality. To address this acute need, healthcare systems have shifted resources and personnel away from non-essential activities, including elective procedures, towards management of the respiratory complications of COVID-19. Over 28,000,000 confirmed cases and 917,000 deaths worldwide later, we finally reached and passed an apparent peak in the number of new cases and are now on an apparent extended plateau. In response, the conversation has shifted away from the acute management of COVID-19 towards re-introduction of routine clinical activities; however, significant caution is needed given the high transmissibility of the virus and the current state of diagnosis, treatment, and vaccination.

Even among the most heavily affected geographies, the proportion of the population that has already been infected may still be well below that required for herd immunity. The proportion needed to achieve herd immunity is a function of the viral reproductive number (Rt). With estimates of Rt generally ranging from 2 to 5, most estimates of the proportion required for herd immunity range from 50% to 80%, compared to estimated infection rates of around 15-20% in areas with the highest incidence, such as New York and Germany. Given the delayed time course for vaccine development, dearth of effective treatments, and issues with testing capacity, we may experience a prolonged curve with multiple peaks as social distancing measures are cyclical implemented. Healthcare workers are among the highest risk groups for SARS-CoV-2 infection, and otolaryngologists are at particularly high risk from exposure to aerosolizing procedures such as sinus surgery. To mitigate these risks, there is an urgent need for protective equipment in aerosolizing procedures.

SUMMARY

The present disclosure provides systems and methods for protecting doctors and others from pathogenic microorganisms aerosolized from patients' mucosal surfaces while undergoing surgical and other procedures.

In an aspect, the present disclosure provides a system comprising: a facial adapter configured to conform to a first portion of a face of a subject during a procedure; a facial shield coupled to the facial adapter, the facial shield comprising at least one access port configured to allow access to at least a second portion of the face during the procedure; and a suction port coupled to at least one of the facial adapter and the facial shield, the suction port configured for connection to a suction source. In various embodiments, the facial adapter, the facial shield, and a surface of the face enclosed by the facial adapter define a partially-enclosed chamber. In various embodiments, when the device is connected to the suction source, the partially-enclosed chamber has a pressure less than 10 Pascals (Pa) below a pressure of an environment surrounding the face. In various embodiments, when the device is connected to the suction source, the partially-enclosed chamber is substantially pneumatically isolated from an environment surrounding the face. In various embodiments, when the device is connected to the suction source, a rate of release of pathogenic particles expelled into an environment surrounding the face is reduced by a factor of at least 2 as compared to a situation in which the device is not connected to the suction source. In various embodiments, at least a portion of the facial shield is substantially transparent. In various embodiments, the facial shield is substantially planar. In various embodiments, the facial shield comprises one or more materials selected from the group consisting of: polymethylmethacrylate (PMMA), polystyrene (PS), general purpose polystyrene (GPPS), styrene acrylonitrile (SAN), styrene methyl methacrylate (SMMA), polycarbonate (PC), high heat polycarbonate (HH-PC), polyethylene terephthalate (PET), polyethylene terephthalate glycol (PET-G), cellulose acetate butyrate (CAB), methyl methacrylate butadiene styrene (MBS), methyl methacrylate acrylonitrile butadiene styrene (MABS), styrene ethylene butylene styrene (SEBS), styrene butadiene copolymer (SB), polyetherimide (PE), polyethersulfone (PES), polysulfone (PSU), cycloolefin copolymer (COC), polylactic acid (PLA), and glass. In various embodiments, the facial adapter is configured to compressively couple to the first portion of the face. In various embodiments, the facial adapter is customized to conform to surface contours of the face. In various embodiments, the facial adapter comprises a silicone or soft plastic polymer cured within a mold. In various embodiments, the mold comprises a three-dimensional (3D) printed material. In various embodiments, the facial adapter is integrally coupled to the facial shield. In various embodiments, the facial adapter is detachably coupled to the facial shield. In various embodiments, the system further comprises a frame configured to couple the facial adapter to the facial shield. In various embodiments, the system further comprises a filter coupled to the suction port. In various embodiments, the access port comprises a cut-out from the facial shield. In various embodiments, the access port comprises a cuttable material. In various embodiments, the facial adapter or the facial shield comprises one or more grooves sized to accommodate one or more members selected from the group consisting of: an endotracheal tube, a temperature probe, and an orogastric tube. In various embodiments, the procedure comprises one or more members selected from the group consisting of: a surgical procedure, a nasal surgical procedure, an oral surgical procedure, a maxillofacial surgical procedure, a dental procedure, an orthodontic procedure, an optometric procedure, and an ophthalmological procedure.

In various embodiments, not all of the depicted components in each figure may be required, and various embodiments may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

Described herein are systems and methods for protecting doctors and others from pathogenic microorganisms aerosolized from patients' mucosal surfaces while undergoing surgical and other procedures. The systems and methods generally operate by forming a partially-enclosed chamber around the patient's face during the procedure. A facial adapter and facial shield isolate a portion of the patient's face from the surrounding environment. The partially-enclosed chamber is connected to a vacuum source, which further decreases the number of pathogenic particles expelled into the environment. The disclosure, however, is not limited to these exemplary embodiments and applications or to the manner in which the exemplary embodiments and applications operate or are described herein.

Figure 1:
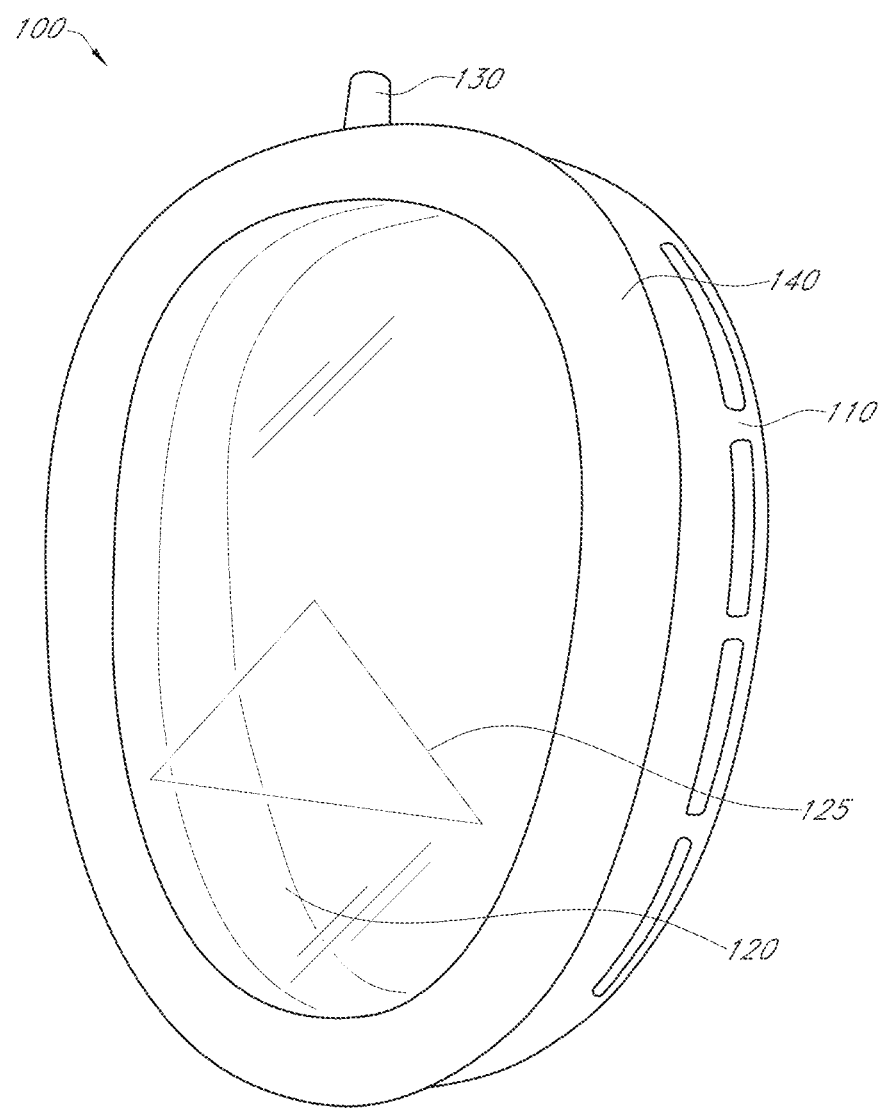
FIG. 1 is a simplified diagram of a first system for protecting parties near a subject during an aerosolizing procedure, in accordance with various embodiments.

FIG. 1 is a simplified exemplary diagram of a system 100 for protecting parties near a subject (such as a patient) during an aerosolizing procedure, in accordance with various embodiments. According to various embodiments, the system 100 can comprise a facial adapter 110, a facial shield 120, and a suction port 130 coupled to one or both of the facial adapter and the facial shield. The system may be configured to fit a portion of a face of a subject during an aerosolizing procedure. The facial adapter, the facial shield, and a surface of the face enclosed by the adapter may define an at least partially-enclosed chamber that at least partially isolates the face from a surrounding environment. Isolating the face in this manner may reduce risk of exposure to pathogenic microorganisms during an aerosolizing procedure. The risk of exposure may be reduced for physicians, other medical personnel, or other people who may be nearby, such as other patients, healthcare workers, or staff in a hospital. Indeed, reduction in the risk of exposure to other hospital patients may be especially important for diseases (such as COVID-19) that disproportionately impact those with pre-existing conditions.

The system 100 may reduce the risk of exposure to a variety of pathogens, including viruses and bacteria. The system may reduce the risk of exposure to coronaviruses, including severe acute respiratory syndrome (SARS) coronavirus (SARS-CoV), SARS-CoV-2, rhinoviruses, influenza viruses, parainfluenza viruses, respiratory syncytial viruses, adenoviruses, parvoviruses, coxsackieviruses, togaviruses, reoviruses, orthomyxoviruses, morbilliviruses, varicella viruses, arenaviruses, filoviruses, poxviruses, paramyxoviruses, *Streptococcus* bacteria, *Staphylococcus* bacteria, *Mycobacterium* bacteria, *Pseudomonas* bacteria, *Acinetobacter* bacteria, Clostridia bacteria, Legionellae bacteria, *Francisella* bacteria, *Bordetella* bacteria, *Mycoplasma* bacteria, *Chlamydia* bacteria, *Klebsiella* bacteria, *Haemophilus* bacteria, *Actinomyces* bacteria, *Enterobacter* bacteria, *Enterococcus* bacteria, and *Corynebacteria* bacteria among others.

In accordance with various embodiments, the facial adapter 110 can be configured to conform to a first portion of a face of a subject during a procedure. The facial adapter may be configured to compressively couple to the first portion of the face. For instance, the facial adapter may comprise a material (such as a silicone) that can be compressed. In this manner, the facial adapter may act as a gasket between the facial shield and the face, helping to further isolate the face from the surrounding environment. The facial adapter may be customized to conform to surface contours of the face of a particular subject. For instance, the facial adapter may comprise a silicone three-dimensional (3D) printed or cured within a mold, which may be a 3D printed mold. The 3D printed mold may be manufactured to allow a good fit to the patient's face.

The facial adapter 110 may comprise one or more grooves (not shown in FIG. 1) sized to accommodate various tubes for the procedure, such as an endotracheal tube, temperature probe, or orogastric tube.

Figure 2:
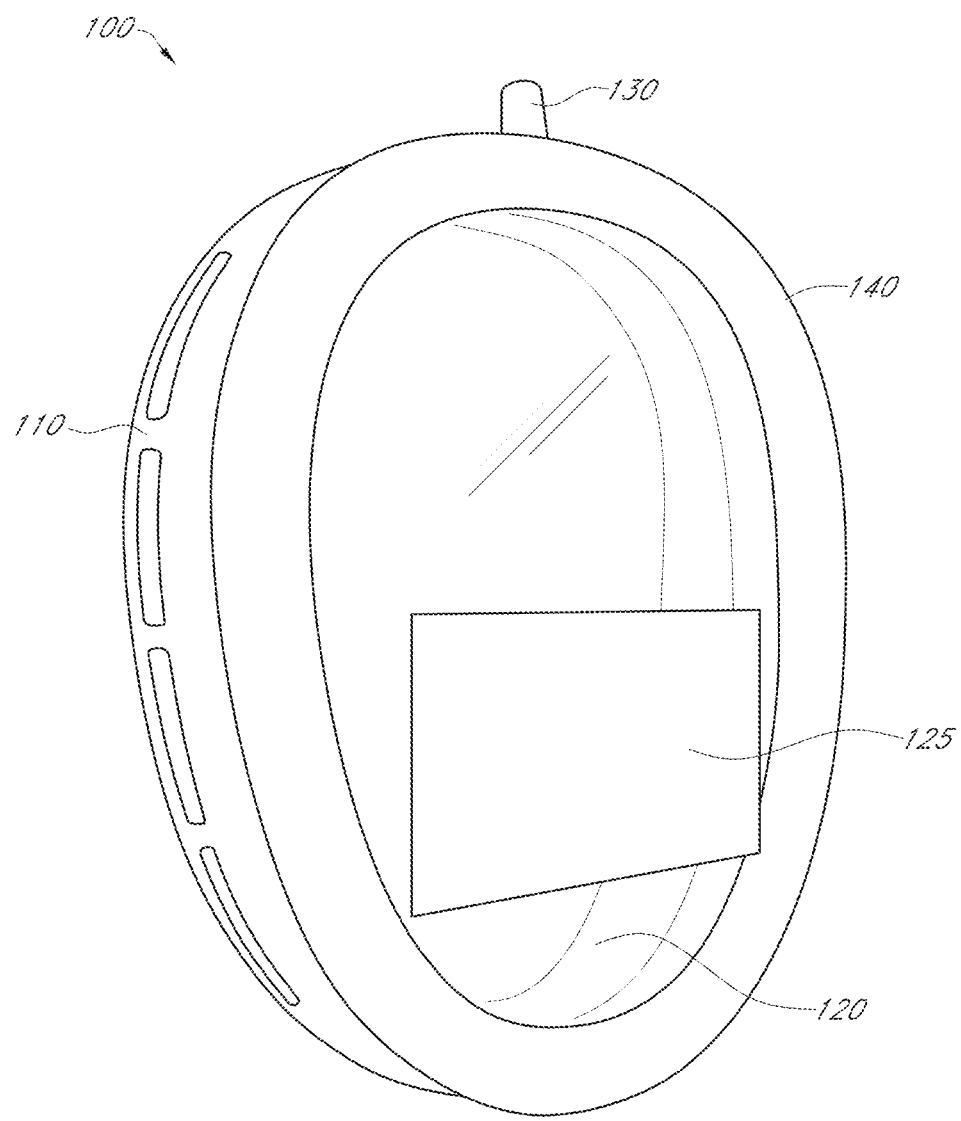
FIG. 2 is a simplified diagram of a second system for protecting parties near a subject during an aerosolizing procedure, in accordance with various embodiments.

In accordance with various embodiments, the facial shield 120 can comprise at least one access port 125 configured to allow access to at least a second portion of the face during the procedure. The access port may allow a person performing the procedure to access the area of the face where the procedure is taking place while still providing a decreased risk of exposure to pathogens. The access port may comprise a cut-out from the facial shield. For instance, the access port may comprise a section of material that has been cut away from the material of the facial shield, as shown in FIG. 1. The access port may comprise a cuttable material (such as a silicone) that the person performing the procedure cuts away according to their preferences for the procedure, allowing the person performing the procedure to customize the access port for the procedure, as shown in FIG. 2. The access port may comprise a regular or irregular shape. For instance, the access port may comprise a generally rectilinear shape, a polygonal shape, a triangular shape, a quadrilateral shape, a rectangular shape, a square shape, a generally curvilinear shape, an elliptical shape, a circular shape, or any other shape.

The facial shield 120 may be substantially planar. At least a portion of the facial shield may be substantially transparent to allow a clear line of sight to the face during the procedure, in accordance with various embodiments. For instance, about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more of the facial shield may be substantially transparent. For instance, about 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less of the facial shield may be substantially transparent. A portion of the face shield that is within a range of any two of the preceding values may be substantially transparent. For instance, 40% to 80% of the facial shield may be substantially transparent, 40% to 60% of the facial shield may be transparent, or 60% to 80% of the facial shield may be transparent. In accordance with various embodiments, the entirety of the face shield may be substantially transparent. The use of a face shield that is at least partially substantially transparent may allow medical personnel performing the procedure to enjoy optical access to the procedure.

The facial shield may comprise a plastic or glass material. For instance, the facial shield may comprise one or more materials selected from the group consisting of: polymethylmethacrylate (PMMA), polystyrene (PS), general purpose polystyrene (GPPS), styrene acrylonitrile (SAN), styrene methyl methacrylate (SMMA), polycarbonate (PC), high heat polycarbonate (HH-PC), polyethylene terephthalate (PET), polyethylene terephthalate glycol (PET-G), cellulose acetate butyrate (CAB), methyl methacrylate butadiene styrene (MBS), methyl methacrylate acrylonitrile butadiene styrene (MABS), styrene ethylene butylene styrene (SEBS), styrene butadiene copolymer (SB), polyetherimide (PE), polyethersulfone (PES), polysulfone (PSU), cycloolefin copolymer (COC), polylactic acid (PLA), and glass.

The facial shield 120 may comprise one or more grooves (not shown in FIG. 1) sized to accommodate various tubes for the procedure, such as an endotracheal tube, temperature probe, or orogastric tube.

The facial shield 120 may be integrally coupled to the facial adapter 110. The facial shield may be detachably coupled to the facial adapter (for instance, using bolts, screws, nails, glue, or other fasteners). The facial shield and the facial adapter may be coupled together by a frame 140.

In accordance with various embodiments, the suction port 130 can be configured for connection to a suction source (not shown in FIG. 1). For example, the suction port 130 may be configured for connection to a vacuum source, such as a vacuum source that may be easily accessible at a hospital or clinic. When the system 100 is connected to the suction source through the suction port 130, the partially-enclosed chamber may be substantially pneumatically isolated from an environment surround the face. When the system 100 is connected to the suction source through the suction port 130, the partially-enclosed chamber may have a pressure that is below a pressure of the environment surrounding the face. For example, the partially-enclosed chamber may have a pressure that is at least about 1 Pascal (Pa), 2 Pa, 3 Pa, 4 Pa, 5 Pa, 6 Pa, 7 Pa, 8 Pa, 9 Pa, 10 Pa, 20 Pa, 30 Pa, 40 Pa, 50 Pa, 60 Pa, 70 Pa, 80 Pa, 90 Pa, 100 Pa, 200 Pa, 300 Pa, 400 Pa, 500 Pa, 600 Pa, 700 Pa, 800 Pa, 900 Pa, 1 kilopascal (kPa), 2 kPa, 3 kPa, 4 kPa, 5 kPa, 6 kPa, 7 kPa, 8 kPa, 9 kPa, 10 kPa or more below the pressure of the environment surrounding the face. The partially-enclosed chamber may have a pressure that is at most about 10 kPa, 9 kPa, 8 kPa, 7 kPa, 6 kPa, 5 kPa, 4 kPa, 3 kPa, 2 kPa, 1 kPa, 900 Pa, 800 Pa, 700 Pa, 600 Pa, 500 Pa, 400 Pa, 300 Pa, 200 Pa, 100 Pa, 90 Pa, 80 Pa, 70 Pa, 60 Pa, 50 Pa, 40 Pa, 30 Pa, 20 Pa, 10 Pa, 9 Pa, 8 Pa, 7 Pa, 6 Pa, 5 Pa, 4 Pa, 3 Pa, 2 Pa, 1 Pa, or less below the pressure of the environment surrounding the face. The partially enclosed-chamber may have a pressure that is within a range defined by any two of the preceding values.

This reduced pressure may reduce a rate at which pathogenic particles are expelled into the environment surrounding the face in comparison to a situation in which the device is not connected to the suction source through the suction port. For instance, when the device is connected to the suction source, the rate of release of pathogenic particles expelled into the environment surrounding the face may be reduced by a factor of at least about 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, or more compared to the situation in which the device is not connected to the suction source. The rate of release of pathogenic particles expelled into the environment surrounding the face may be reduced by a factor of at most about 100, 90, 80, 70, 60, 50, 40, 30, 20, 10, 9, 8, 7, 6, 5, 4, 3, 2, 1.9, 1.8, 1.7, 1.6, 1.5, 1.4, 1.3, 1.2, 1.1, or less compared to the situation in which the device is not connected to the suction source. The rate of release of pathogenic particles expelled into the environment surrounding the face may be reduced by a factor that is within a range defined by any two of the preceding values.

In accordance with various embodiments, the system 100 can comprise a filter (not shown in FIG. 1) coupled to the suction port 130. The filter may capture pathogenic particles before they are sucked through the suction port and into the suction source and prevent the pathogenic particles from spreading out of the partially-enclosed chamber. Alternatively or in combination, the suction source itself may comprise a filter to capture the pathogenic particles.

The system 100 may be utilized to reduce the risk of exposure to pathogens for a variety of individuals, such as surgeons, doctors, nurses, other hospital or clinical personnel, dentists, dental assistants, optometrists, ophthalmologists, other patients in hospitals or clinics, and the general public. The system may be utilized in a variety of procedures, such as a surgical procedure, a nasal surgical procedure, an oral surgical procedure, a maxillofacial surgical procedure, a dental procedure, an orthodontic procedure, an optometric procedure, or an ophthalmological procedure.

Figure 3:
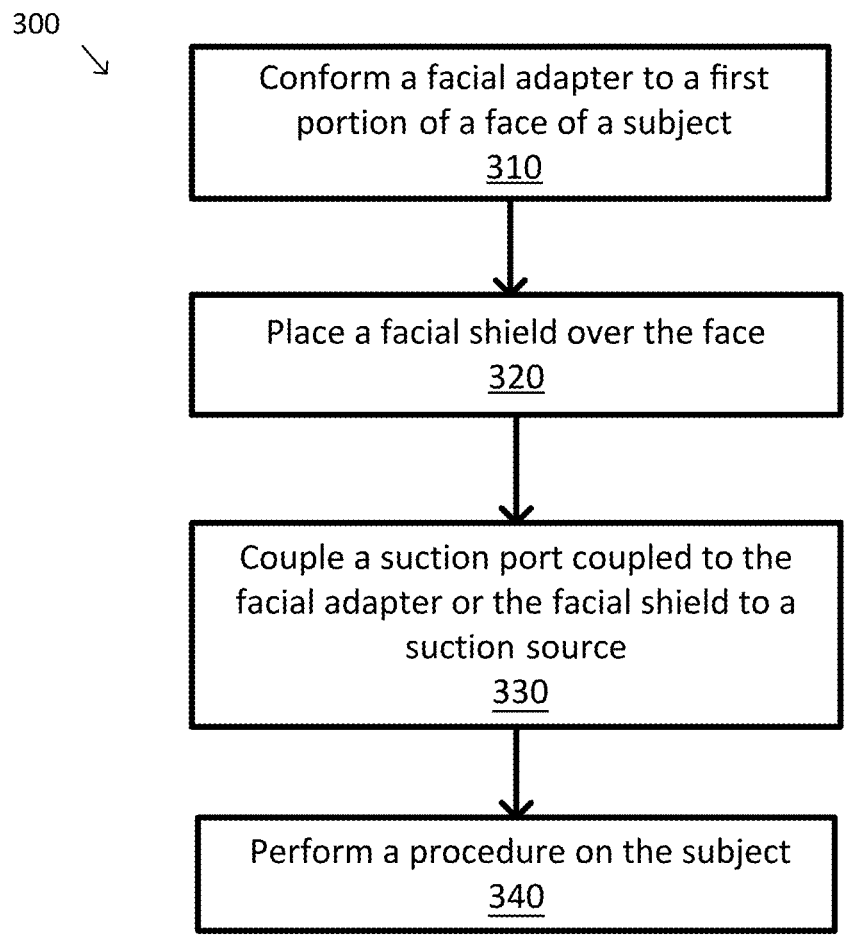
FIG. 3 is a simplified diagram of a method for protecting parties near a subject during an aerosolizing procedure, in accordance with various embodiments.

FIG. 3 is a simplified diagram of a method 300 for protecting parties near a subject during an aerosolizing procedure. In accordance with various embodiments, the method 300 can comprise a step 310 of conforming a facial adapter to a first portion of a face of a subject, a step 320 of placing a facial shield over the face, a step 330 of coupling a suction port coupled to the facial adapter or the facial shield to a suction source, and a step 340 of performing a procedure on the subject. The facial adapter, facial shield, and suction port may be similar to any facial adapter, facial shield, and suction port described or contemplated herein (for instance, with respect to FIG. 1 or FIG. 2), or any designs reasonably related thereto.

It should also be appreciated that any operation, sub-operation, step, sub-step, process, or sub-process of method 300 may be performed in an order or arrangement different from the embodiments illustrated by FIG. 3. For example, in other embodiments, one or more operations may be omitted or added.

EXAMPLES

Example 1: Use of Face-Mounted, Negative-Pressure Antechamber in Endoscopic Basal Skull Surgery Computer modeling, 3D printing, and silicone molding were utilized to develop a device that met the following criteria: 1) an enclosed, negative pressure compartment, 2) an access port for surgical instrumentation that could be altered by the surgeon to meet the needs of the procedure, 3) a flexible adapter to achieve a seal when mounted on the face over an endotracheal tube, and 4) a transparent shield. Negative pressure was achieved by attaching the assembly to a suction source, such as a Neptune smoke evacuation system (Stryker, Kalamazoo, Mich.). The device was attached to the face using elastic hooks, which were secured against a Mayfield headrest. The flexible adapter featured a cutout for the endotracheal tube to minimize disruption of the negative pressure seal.

Computerized model design was performed in Blender version 2.82. Three-dimensional models were prepared using slicing software, Ultimaker Cura version 4.5, and printed on a Creality Ender 3 with polylactic acid (PLA). Using the device frame as a template, a transparent shield was cut from a 3-mm thick acrylic plate after confirmation of the appropriate dimensions by the surgeons. Molds for the silicone gasket and diaphragm were designed in Blender and printed with a Creality Ender 3 after preparation in Ultimaker Cura. Smooth-on brand silicone (Dragon Skin 20) was prepared per manufacturer's instructions and poured into the assembled molds. Models were prototyped with 3D-printing with intent to transition production to injection molding to optimize cost and time effectiveness, standardization, and sterility.

Figure 4:
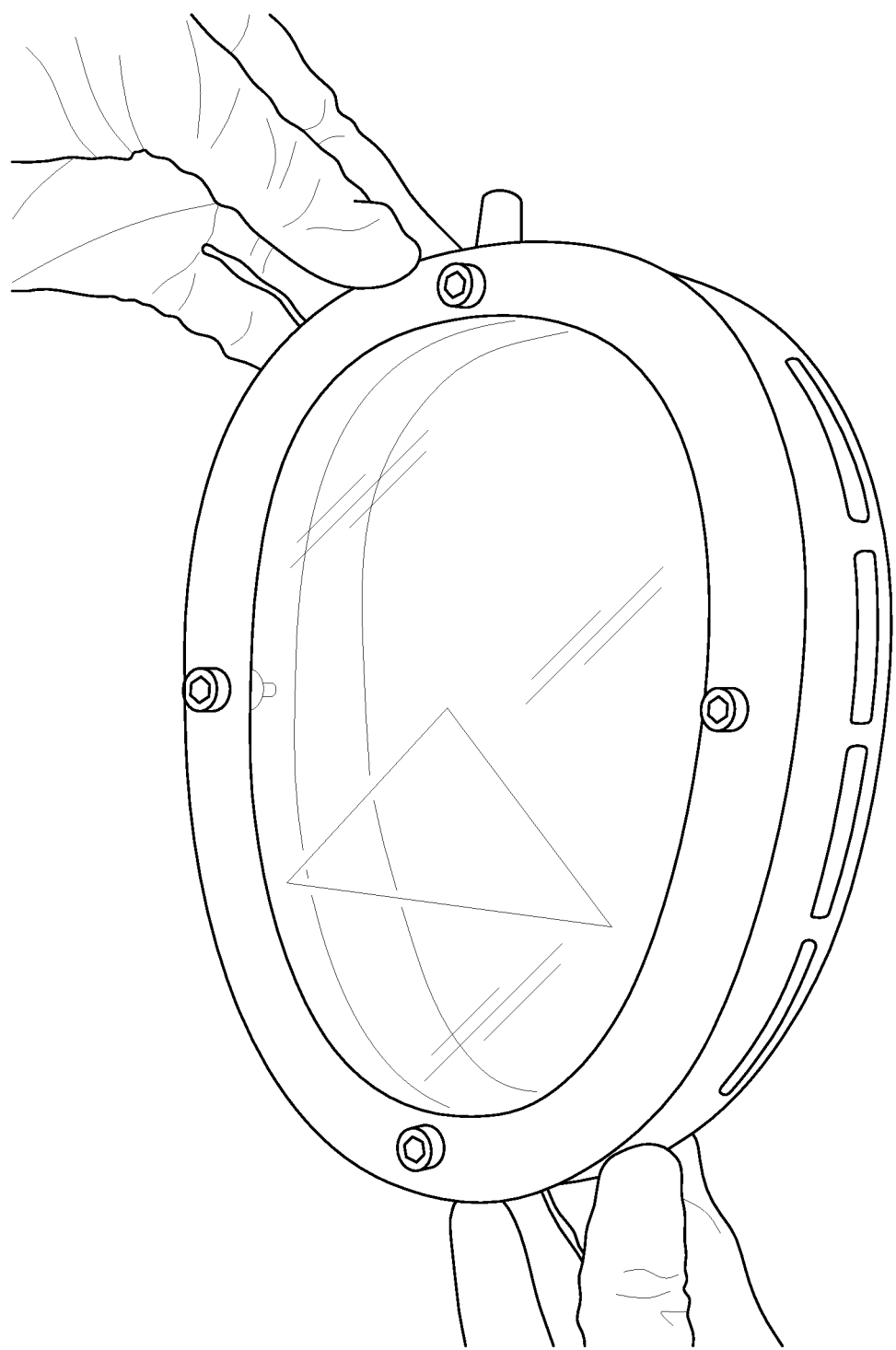
FIG. 4 shows a device featuring a triangular cutout in an acrylic shield at the level of the nares, in accordance with various embodiments.
Figure 5:
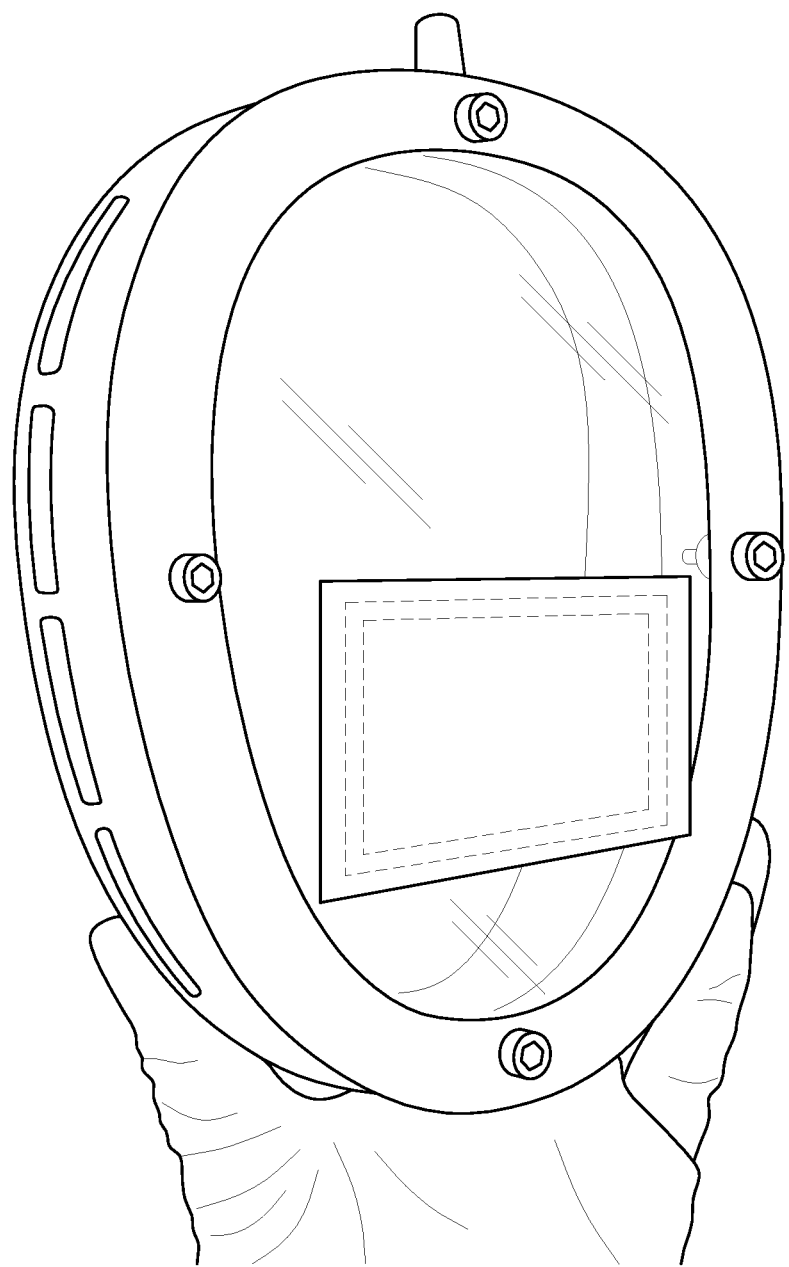
FIG. 5 shows a device featuring a rectangular cutout situated further inferiorly and covered by a silicone diaphragm, in accordance with various embodiments.
Figure 6:
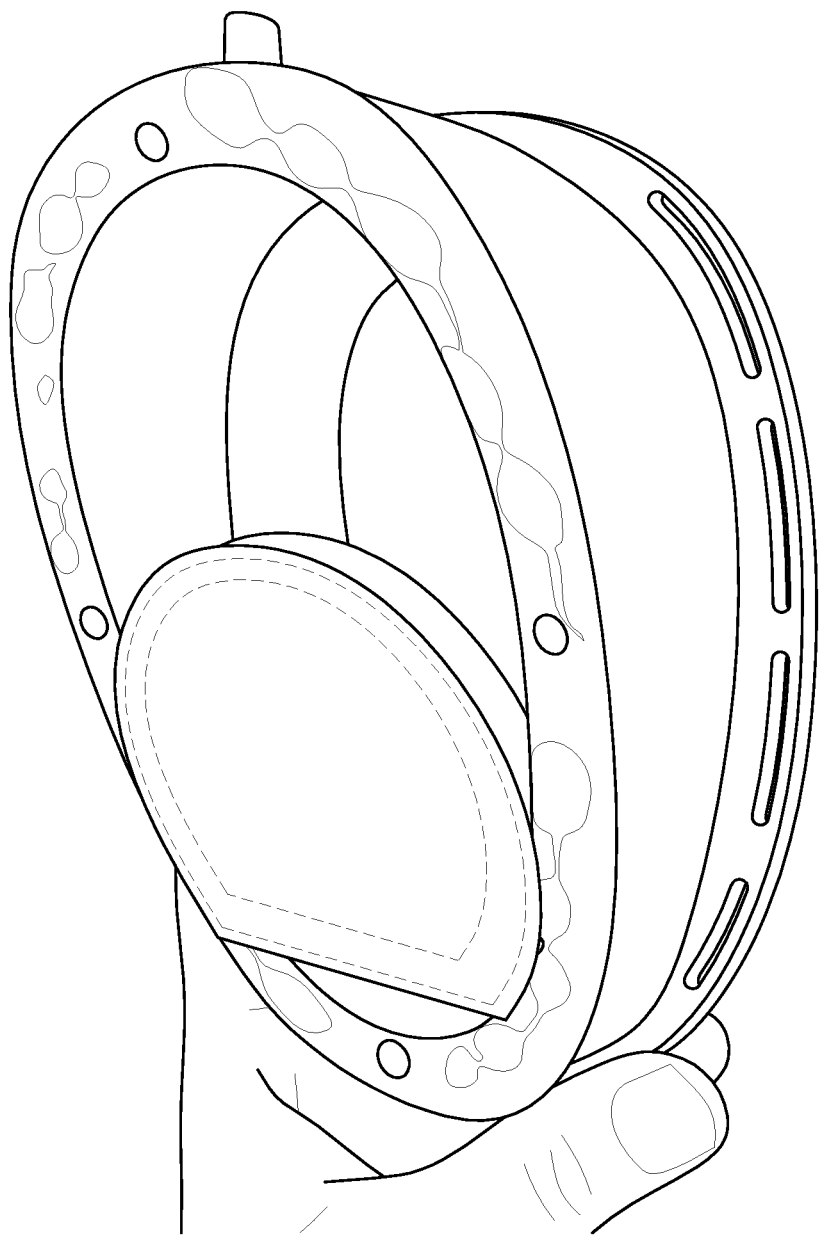
FIG. 6 shows a device featuring a rounded top to the diaphragm to accommodate larger noses found in acromegaly and a tapered design with a lower profile near the chin, in accordance with various embodiments.

Iterative changes were made in the design of the device based on the feedback of the physicians and other. A first version of the device included a triangular cutout in the acrylic shield at the level of the nares, as shown in FIG. 4. A second version utilized a rectangular cutout situated further inferiorly in the acrylic shield as compared to the first version and covered by a silicone diaphragm to maximize negative pressure within the confines of the chamber, as shown in FIG. 5. A third version included a rounded top to the diaphragm, as shown in FIG. 6. This rounded top design could, for example, accommodate larger noses found in acromegaly. The third version also included a tapered design with a lower profile near the chin, as shown in FIG. 6. This tapered design could, for example, bring the instruments closer to the face and nares. Vertical slits could be created in the diaphragm with a surgical blade at the beginning of surgery to allow for passage of instruments. The third version could feature a semicircular cutout for instruments along with a lower profile at the chin, which could, for example, bring the surgeons' hands closer to the nares to allow to improve surgical maneuverability and not compromise instrument length.

Efficacy of the devices was assessed using several different techniques. First, a vapor clearance test utilizing the second iteration of the device and a 3D-printed face with an open aperture at the level of the nasal cavity was performed. The chamber was injected with vaporized glycerin and water, filling its internal volume of approximately 1,300 cc. Next, negative pressure was applied by connecting the device to suction and the time to clear the chamber was measured. The suction source in this model was provided by an SMR Maxi Cabinet (Global Surgical Corporation, Saint Louis, Mo.), which is commonly used in outpatient otolaryngology offices. Pressure within the tube (relative to atmospheric pressure) was measured using a RISEPRO manometer (UPC: 712201953381) connected to a t-tube placed between the vacuum pump and the device, approximately 10 cm away from the chamber. Tube pressure was chosen as a surrogate for vacuum strength as pressures delivered by vacuums depend on features of the vacuum tubing, such as length and surface roughness. Pressure within the chamber relative to the atmosphere was measured with the manometer probe placed 2 cm in through the side of the chamber. With this setup, a pressure of −0.14 cm $H_2O$ was achieved within the chamber. The clearance time was defined as the time from full saturation of the chamber to the point of no visible vapor. Visualization of the vapor stream was augmented by use of blue light. Clearance time was used to calculate air flow and air exchange.

Figure 7A:
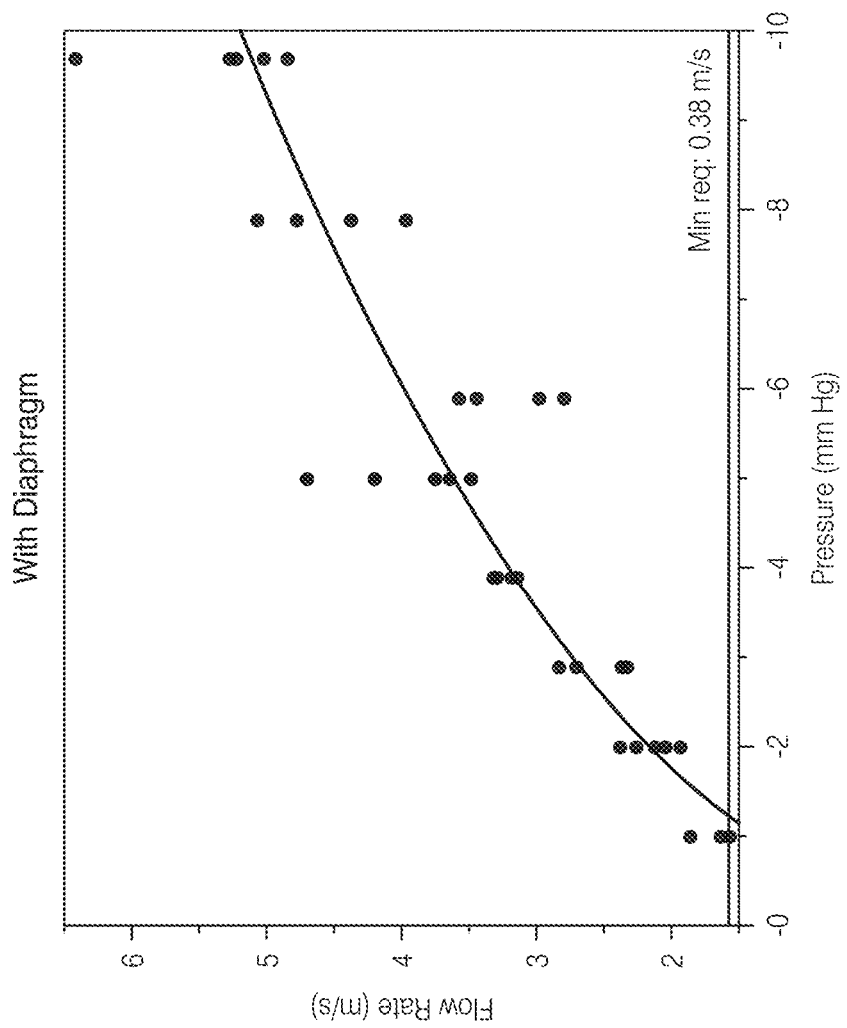
FIG. 7A shows flow rates as a function of pressure for identification of the lowest vacuum setting needed to meet specifications for class I biosafety cabinets for a device with a diaphragm, in accordance with various embodiments.
Figure 7B:
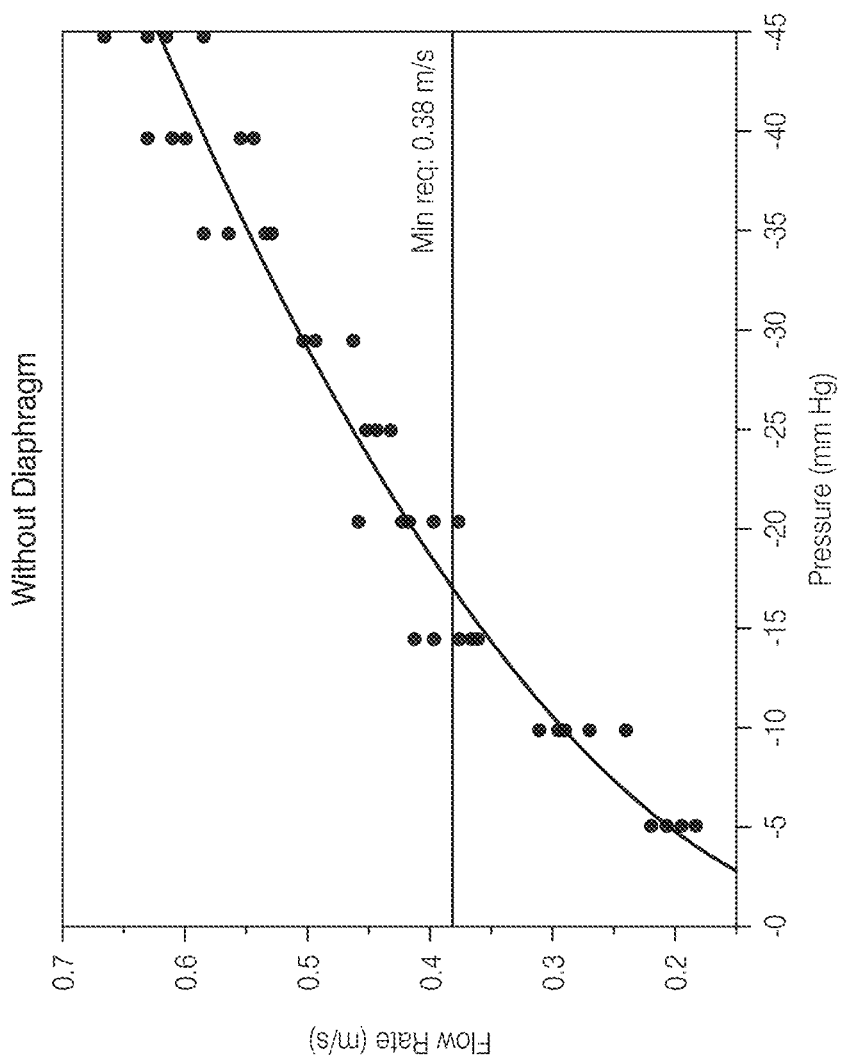
FIG. 7B shows flow rates as a function of pressure for identification of the lowest vacuum setting needed to meet specifications for class I biosafety cabinets for a device without a diaphragm, in accordance with various embodiments.
Figure 8A:
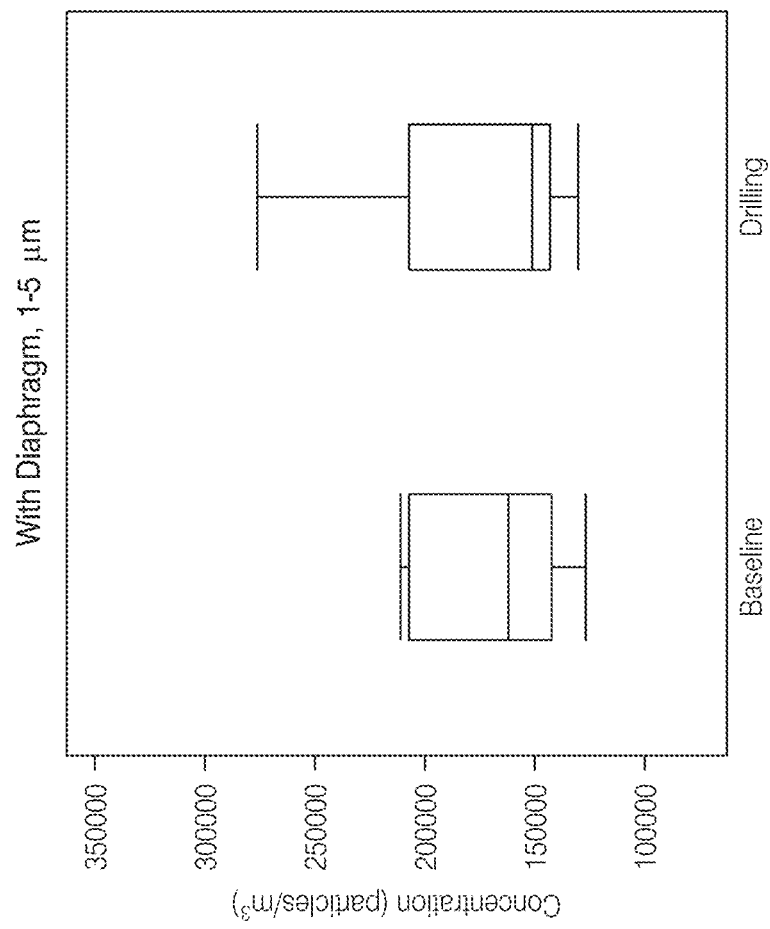
FIG. 8A shows 1-5 μm particle counts at baseline compared to drilling for a device with a silicone diaphragm, in accordance with various embodiments.
Figure 8B:
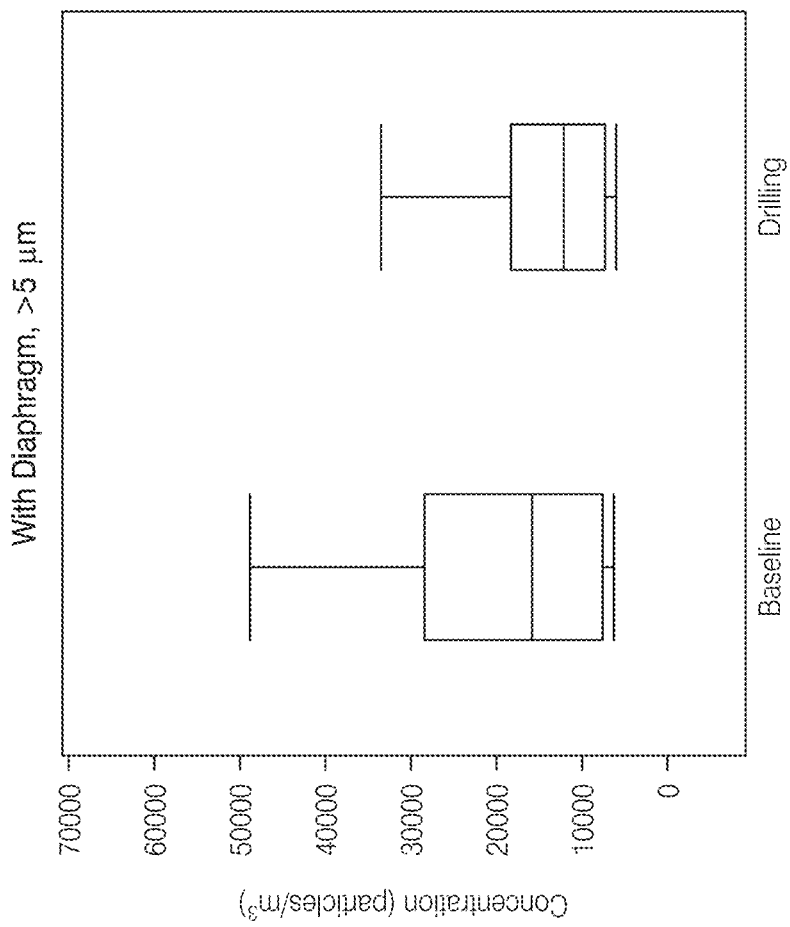
FIG. 8B shows >5 μm particle counts at baseline compared to drilling for a device with a silicone diaphragm, in accordance with various embodiments.
Figure 8C:
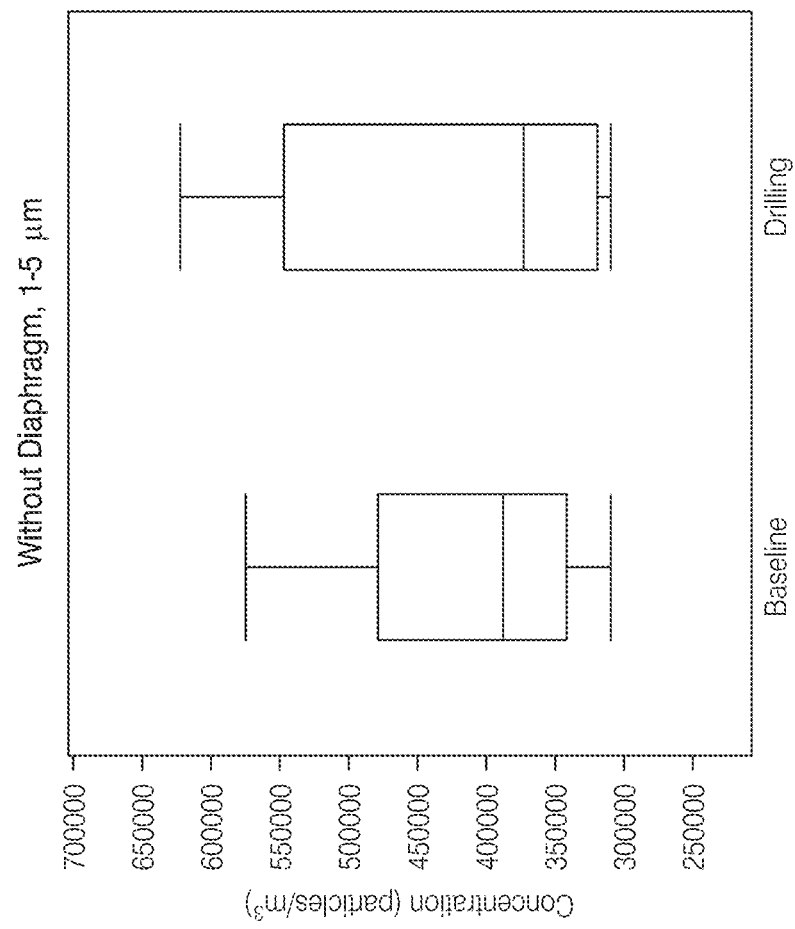
FIG. 8C shows 1-5 μm particle counts at baseline compared to drilling for a device without a silicone diaphragm, in accordance with various embodiments.
Figure 8D:
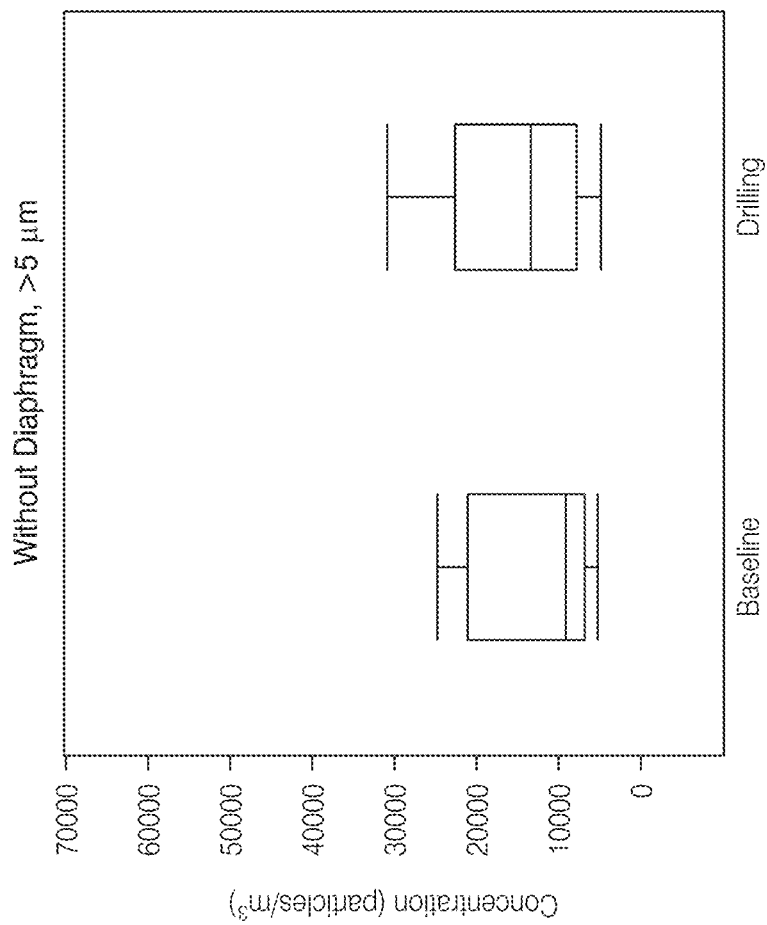
FIG. 8D shows >5 μm particle counts at baseline compared to drilling for a device without a silicone diaphragm, in accordance with various embodiments.

FIGS. 7A and 7B show flow rates as a function of pressure for identification of a vacuum setting for meeting specifications associated with class I biosafety cabinets. The device with and without the diaphragm required −1.0 mm Hg and −14.5 mm Hg, respectively, to achieve average flow rates above specifications. Drilling ovine ribs at 75,000 rpm generated an average of 21,488 particles between 1-10 micrometers (μm) per minute (95% confidence interval, CI: 11,822-31,155). At the lowest possible vacuum setting needed to meet specifications for class I biosafety cabinets, there were no significant differences between particle counts at baseline compared to drilling for devices with and without the silicone diaphragm, as shown in FIGS. 8A, 8B, 8C, and 8D.

Figure 9A:
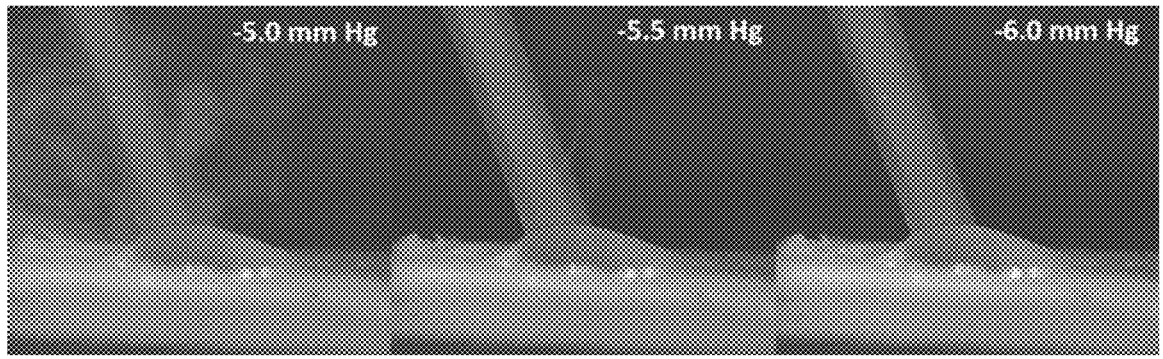
FIG. 9A shows high-speed a videography estimate of the higher thresholds required to contain aerosols for a device with a silicone diaphragm, in accordance with various embodiments.
Figure 9B:
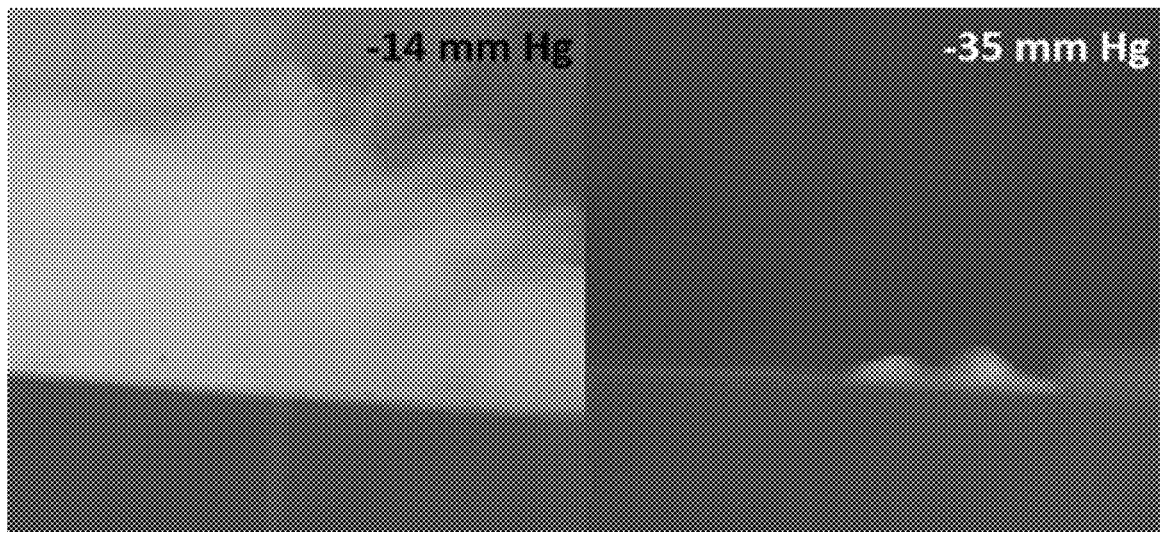
FIG. 9B shows high-speed a videography estimate of the higher thresholds required to contain aerosols for a device with a silicone diaphragm, in accordance with various embodiments.

However, high-speed videography estimated higher thresholds required to contain aerosols, at −6 mm Hg and −35 mm Hg for the devices with and without the silicone diaphragm, as shown in FIG. 9A and FIG. 9B, respectively. These thresholds were confirmed by shadowography. Simulation of movement at the operative port for the open-faced model, however, disrupted aerosol containment. For the closed-faced model, flow rate at minimum vacuum power identified by videography was 4.0±0.1 meters per second (m/s), volume flow rate 0.40±0.01 liters per second (L/s), chamber pressure relative to atmosphere—0.15±0.01 millimeters mercury (mm Hg), and time to 99.9% clearance 16.2±0.7 seconds. For the open-faced model, flow rate was 0.51±0.01 m/s, volume flow rate 1.73±0.02 L/s, and time to 99.9% clearance 3.69±0.05 seconds. Pressure in the open-faced chamber was too low to be detected.

Efficacy of the device was subsequently assessed utilizing an optical particle sizer (OPS) [AeroTrak 9306, TSI Incorporated; Shoreview, Minn.] to quantify the amount of particles produced during endonasal surgery under various conditions. This assay was performed first in a human cadaver and then in the operating room after obtaining IRB approval. In the cadaver model, a complete sphenoethmoidectomy and bilateral middle turbinate resection were performed in a fixed, latex-injected human cadaver head, followed by a posterior septectomy. Next, the rostrum of the sphenoid was drilled under controlled conditions utilizing a 4 millimeter (mm) cutting burr at 75,000 revolutions per minute (rpm). The isokinetic inlet of the OPS was placed approximately 15 centimeters (cm) away from the face, and particle counts were collected every 30 seconds. Baseline counts were obtained in absence of drilling, along with counts during drilling without the device and drilling with the device, with and without the silicone diaphragm. Drilling commenced for 30 seconds, with a 2-minute washout period between measurements, which were repeated in triplicate. For data analysis, particles were stratified by size: ≤5 micrometers (μm) and >5 μm.

Clinical feasibility and efficacy of the device was then assessed in 6 endoscopic endonasal skull base procedures. Particle counts were collected during endoscopic drilling with a 15-degree 4 mm cutting and diamond skull base burr for 3 of the 6 cases. In these instances, readings were taken every 30 seconds to 1 minute, and the isokinetic in the inlet of the OPS was placed as closed to the surgical field as possible without breaking sterility. Patient electronic medical records were accessed to retrospectively collect information, including demographic details, operative time, and pathologic diagnosis. Patients were also contacted by telephone or directly during office visits between 1 to 2 weeks after surgery and queried about potential complications related to use of the device, including facial deformity or discomfort.

Express consent was obtained from patients for intraoperative photography and use of the images for research purposes. Statistical analysis, including Kruskal-Wallis one-way analysis of variance with post-hoc Mann-Whitney pairwise comparison, was performed using SPSS 26 (IBM; Armonk, N.Y.).

The vapor clearance test demonstrated efficacy of the device under experimental conditions. There was no visible escape of vapor around the silicone gasket or through the diaphragm. Clearance time was approximately 5 seconds, corresponding to a flow rate of 2.1 cubic feet per minute. The corresponding air change rate was 2,818 air changes per hour.

Kruskal-Wallis testing revealed a statistically significant difference (p=0.05) in median particle counts (≤5 μm) between the following experimental conditions: baseline (without drilling), drilling with face uncovered, drilling with device and diaphragm, drilling with device without diaphragm. Drilling of the sphenoid bone resulted in a statistically significant 2.49-fold increase (p=0.001) in particles≤5 μm compared to baseline on post-hoc pairwise testing. Use of the device led to return of counts to baseline, both with and without the presence of the silicone diaphragm, as shown in Table 1. In contrast, there was no statistically significant difference in the counts of particles>5 μm (p=0.255) under the same set of conditions.

TABLE 1

Particle data from cadaver model

| Intervention | N | 1-5 μm Median concentration (particles/m$^3$) | p-value | 5 μm Median concentration (particles/m$^3$) | p-value |
| --- | --- | --- | --- | --- | --- |
| Baseline | 20 | 305,634 | | 13,028 | |
| Without device | 3 | 760,563 | 0.001** | 11,268 | 0.763 |
| With device and diaphragm | 3 | 300,000 | 1.000 | 11,268 | 0.196 |
| With device, without diaphragm | 3 | 304,225 | 0.514 | 7,042 | 0.094 |

\* p < 0.05,
\*\*p < 0.01

The system was utilized for endoscopic skull base surgery (ESBS) in 6 patients. All patients were asymptomatic and had tested negative for SARS-CoV-2 within 24 hours of surgery. Nevertheless, personal protective equipment (PPE) was worn, including N95 masks and face shields given the possibility of a false negative test. Indications for surgery and clinical course are detailed below.

Patient 1: 61-year-old female with an enhancing lytic lesion involving the vertebral body of C2 and clivus with erosion of floor of the sphenoid sinus and associated extraosseous extension into the prevertebral soft tissues, concerning for metastasis. Positron emission tomography (PET) and x-ray computed tomography (CT) demonstrated two right hypermetabolic renal masses. Preoperative angiography was performed due to the presumptive diagnosis of metastatic renal cell carcinoma, typically a highly vascular tumor, but there was minimal tumor blush, so no embolization was ultimately performed. The patient subsequently underwent endoscopic clival resection without complication. She recovered well after surgery and was discharged home on post-operative day (POD) 2. Post-operative magnetic resonance imaging (MRI) scan revealed a gross total resection of the tumor. Final histopathology revealed keratinizing squamous cell carcinoma, suggestive of primary nasopharyngeal carcinoma.

Patient 2: 68-year-old female with progressive bitemporal hemianopsia and a 3.7 cm×3.2 cm×2.2 cm pituitary lesion with suprasellar extension and internal hemorrhage with severe compression of the optic chiasm and associated optic nerve atrophy. Preoperative endocrine evaluation demonstrated mild central hypothyroidism and hyponatremia. The patient underwent endoscopic endonasal transsphenoidal resection of her presumed macroadenoma without complication. Postoperative MRI demonstrated a gross total resection with complete decompression of the optic apparatus. The patient was discharged uneventfully on POD 3 with subjective improvement in her vision. Final histopathology revealed pituitary adenoma with negative hormone staining on immunohistochemistry.

Patient 3: 51-year-old female with remote history of prior transsphenoidal resection of a pituitary macroadenoma and progressive vision loss. Imaging demonstrated inferior descent and herniation of the optic chiasm and apparatus, gyri rectus, and bilateral anterior cerebral arteries in an expanded sella. The patient underwent lumbar drain placement and endoscopic transsphenoidal extradural chiasmapexy with rigid buttress placement. Lumbar drainage was continued for 36 hours postoperatively. Postoperative imaging demonstrated resolution of the herniation of the optic chiasm and apparatus. She was discharged home without issue on POD 2 with her vision subjectively improved.

Patient 4: 69-year-old male with right abducens palsy and right-sided headache, facial pain. Imaging revealed a 2.2 cm×2.6 cm×2.4 cm lobulated mass in the right petrous apex, encasing the right petrous internal carotid artery, and extending to the right cavernous sinus, Meckel's cave, medial temporal lobe, and prevertebral musculature. The patient underwent an endoscopic transsphenoidal, transpterygoid approach to the mass, with mobilization of the right petrous carotid artery to resect the lesion posterior and medial to the artery. He had an uneventful postoperative course and was discharged on POD 1. Postoperative MRI revealed near total resection with residual tumor in the prevertebral musculature and normal right petrous carotid flow void. Final histopathology revealed chordoma.

Patient 5: 60-year-old female with increasing shoe and ring size over the past year and changes in dental occlusion. Laboratory work-up revealed an elevated insulin-like growth factor-1 (IGF-1) and growth hormone (GH), and imaging demonstrated a 3.1 cm sellar and suprasellar mass with compression of the optic chiasm and cavernous sinus extension. The patient was treated with lanreotide for 3 months, after which she underwent endoscopic transsphenoidal resection of her macroadenoma (Table 2). Postoperative MRI demonstrated a gross total resection of the tumor. IGF-1 and GH values were normal on POD 2, and the patient was discharged uneventfully on POD 3.

Patient 6: 53-year-old male with decreased libido, and hot and cold flashes. His symptoms were also initially accompanied by headache. Imaging revealed a bilobed 1.8 cm×1.1 cm×1.1 cm cystic sellar mass with optic chiasm compression. Hormonal testing revealed central hypothyroidism and hypogonadotrophic hypogonadism. The patient underwent endoscopic transsphenoidal drainage of a Rathke's cleft cyst, confirmed intraoperatively by removal of the cyst contents. Postoperative MRI revealed resolution of the lesion. The patient was discharged uneventfully on POD 2.

Figure 10A:
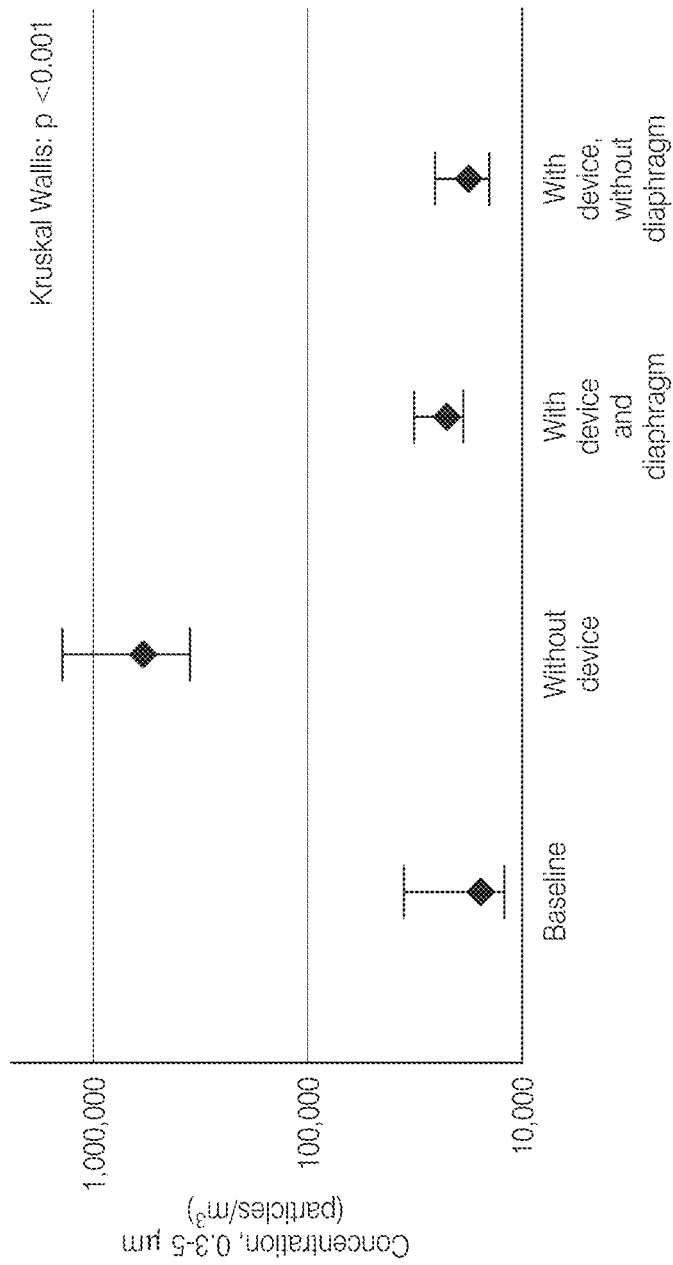
FIG. 10A shows interoperative particle counts for particles having a size between 0.3 micrometers (μm) and 5 μm, in accordance with various embodiments.
Figure 10B:
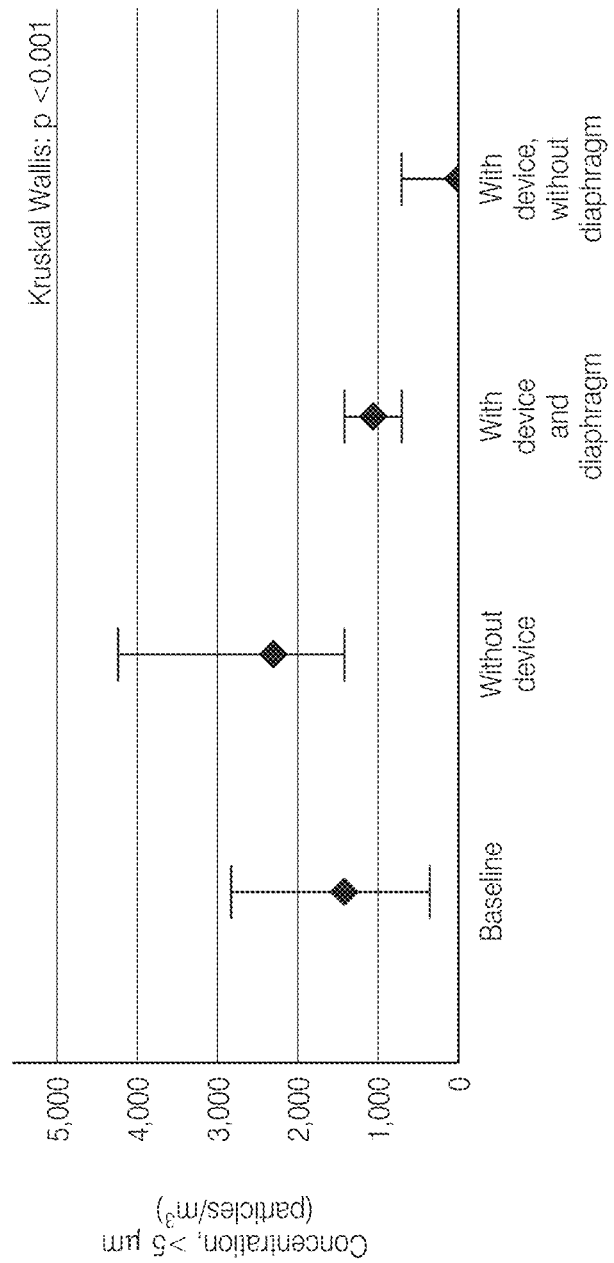
FIG. 10B shows interoperative particle counts for particles having a size great than 5 μm, in accordance with various embodiments.

None of the four surgeons reported significant disruptions by the system in their ability to perform surgery, and none of the patients reported any complications related to use of the device, including facial pain, numbness, or injury, at 1 to 2 weeks postoperatively. Summary data from intraoperative particle counts are displayed in FIG. 10A and FIG. 10B. There was a statistically significant ($p<0.001$) difference between median number particles detected at baseline and during various drilling conditions on Kruskal-Wallis analysis of variance. Compared with baseline (15,548 particles/meter cubed, $m^3$), endoscopic drilling with the face uncovered led to a 37-fold increase in the number of particles≤5 μm (577,739 particles/$m^3$, $p<0.001$). Use of the system led to a reduction in the number of detected particles≤5 μm to 1.43- and 1.14-times baseline with and without the use of the diaphragm ($p=0.13$ and $0.37$). For particles>5 μm, compared with baseline (1,413 particles/$m^3$), endoscopic drilling with the face uncovered led to a 1.6-fold increase in the number of particles (2,297 particles/$m^3$, $p=0.03$). Use of the system led to a reduction in the number of detected particles to 1,060 and 0 particles/$m^3$, with and without the use of the diaphragm, respectively, the latter of which was significantly lower than baseline ($p=0.007$).

The reduction in the number of airborne particles detected by an OPS was treated as a surrogate for efficacy of the device in reducing infectious aerosols during surgery. The device was effective in vitro and in vivo at reducing the number of particles, particularly in the sub-5 μm range. Interestingly, the size of the instrument port did not significantly increase the number of particles detected by the OPS, suggesting that negative pressure, in the strict sense, may not be responsible for the effectiveness of the device. This is supported by intraoperative measurements demonstrating negative flow within the device in absence of measurable negative pressure. Laminar flow of particles out into the exhaust of the device may be chiefly responsible for the reduction in particles detected outside of the device, similar to the mode of action of biosafety cabinets. The data indicated that aerosols elaborated during endoscopic drilling were primarily≤5 μm, and use of the device led to a reduction of particles detected in the same size range. The predominance of particles generated and detected within the sub-5 μm perhaps explains the seemingly disparate results for particles>5 μm between the cadaver and live patients. Overall, endoscopic drilling appears to generate fewer particles>5 μm, which may have limited the ability to detect differences with and without the use of the device.

Recitation of Embodiments

Embodiment 1. A system comprising:
a facial adapter configured to conform to a first portion of a face of a subject during a procedure;
a facial shield coupled to the facial adapter, the facial shield comprising at least one access port configured to allow access to at least a second portion of the face during the procedure; and
a suction port coupled to at least one of the facial adapter and the facial shield, the suction port configured for connection to a suction source.

Embodiment 2. The system of Embodiment 1, wherein the facial adapter, the facial shield, and a surface of the face enclosed by the facial adapter define a partially-enclosed chamber.

Embodiment 3. The system of Embodiment 1 or Embodiment 2, wherein, when the device is connected to the suction source, the partially-enclosed chamber has a pressure less than 10 Pascals (Pa) below a pressure of an environment surrounding the face.

Embodiment 4. The system of any one of Embodiments 1-3, wherein, when the device is connected to the suction source, the partially-enclosed chamber is substantially pneumatically isolated from an environment surrounding the face.

Embodiment 5. The system of any one of Embodiments 1-4, wherein, when the device is connected to the suction source, a rate of release of pathogenic particles expelled into an environment surrounding the face is reduced by a factor of at least 2 as compared to a situation in which the device is not connected to the suction source.

Embodiment 6. The system of any one of Embodiments 1-5, wherein at least a portion of the facial shield is substantially transparent.

Embodiment 7. The system of any one of Embodiments 1-6, wherein the facial shield is substantially planar.

Embodiment 8. The system of any one of Embodiments 1-7, wherein the facial shield comprises one or more materials selected from the group consisting of: polymethylmethacrylate (PMMA), polystyrene (PS), general purpose polystyrene (GPPS), styrene acrylonitrile (SAN), styrene methyl methacrylate (SMMA), polycarbonate (PC), high heat polycarbonate (HH-PC), polyethylene terephthalate (PET), polyethylene terephthalate glycol (PET-G), cellulose acetate butyrate (CAB), methyl methacrylate butadiene styrene (MBS), methyl methacrylate acrylonitrile butadiene styrene (MABS), styrene ethylene butylene styrene (SEBS), styrene butadiene copolymer (SB), polyetherimide (PE), polyethersulfone (PES), polysulfone (PSU), cycloolefin copolymer (COC), polylactic acid (PLA), and glass.

Embodiment 9. The system of any one of Embodiments 1-8, wherein the facial adapter is configured to compressively couple to the first portion of the face.

Embodiment 10. The system of any one of Embodiments 1-9, wherein the facial adapter is customized to conform to surface contours of the face.

Embodiment 11. The system of any one of Embodiments 1-10, wherein the facial adapter comprises a silicone or soft plastic polymer cured within a mold.

Embodiment 12. The system of Embodiment 11, wherein the mold comprises a three-dimensional (3D) printed material.

Embodiment 13. The system of any one of Embodiments 1-12, wherein the facial adapter is integrally coupled to the facial shield.

Embodiment 14. The system of any one of Embodiments 1-12, wherein the facial adapter is detachably coupled to the facial shield.

Embodiment 15. The system of any one of Embodiments 1-14, further comprising a frame configured to couple the facial adapter to the facial shield.

Embodiment 16. The system of any one of Embodiments 1-15, further comprising a filter coupled to the suction port.

Embodiment 17. The system of any one of Embodiments 1-16, wherein the access port comprises a cut-out from the facial shield.

Embodiment 18. The system of any one of Embodiments 1-17, wherein the access port comprises a cuttable material.

Embodiment 19. The system of any one of Embodiments 1-18, wherein the facial adapter or the facial shield comprises one or more grooves sized to accommodate one or more members selected from the group consisting of: an endotracheal tube, a temperature probe, and an orogastric tube.

Embodiment 20. The system of any one of Embodiments 1-19, wherein the procedure comprises one or more members selected from the group consisting of: a surgical procedure, a nasal surgical procedure, an oral surgical procedure, a maxillofacial surgical procedure, a dental procedure, an orthodontic procedure, an optometric procedure, and an ophthalmological procedure.

In describing the various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments. Similarly, any of the various system embodiments may have been presented as a group of particular components. However, these systems should not be limited to the particular set of components, now their specific configuration, communication and physical orientation with respect to each other. One skilled in the art should readily appreciate that these components can have various configurations and physical orientations (e.g., wholly separate components, units and subunits of groups of components, different communication regimes between components).

Although specific embodiments and applications of the disclosure have been described in this specification, these embodiments and applications are exemplary only, and many variations are possible.

What is claimed is:

1. A system comprising:
a facial adapter configured to conform to a first external portion of a face of a subject during a procedure; and
a facial shield comprising at least one access port configured to allow access to at least a second external portion of the face during the procedure, wherein the at least one access port is covered by a silicone diaphragm; and
a suction port disposed directly on the facial adapter, the suction port configured for connection to a suction source.

2. The system of claim 1, wherein the facial adapter, the facial shield, and a surface of the face enclosed by the facial adapter define a partially-enclosed chamber.

3. The system of claim 2, wherein, when the suction port is connected to the suction source, the partially-enclosed chamber has a pressure less than 10 Pascals (Pa) below a pressure of an environment surrounding the face.

4. The system of claim 2, wherein, when the suction port is connected to the suction source, the partially-enclosed chamber is substantially pneumatically isolated from an environment surrounding the face.

5. The system of claim 1, wherein the facial adapter is customized to conform to surface contours of the face.

6. The system of claim 5, wherein the facial adapter comprises a silicone cured within a mold.

7. The system of claim 6, wherein the mold comprises a three-dimensional (3D) printed material.

8. The system of claim 1, wherein, when the suction port is connected to the suction source, a rate of release of pathogenic particles expelled into an environment surrounding the face is reduced by a factor of at least 2 as compared to a situation in which the device is not connected to the suction source.

9. The system of claim 1, wherein at least a portion of the facial shield is substantially transparent.

10. The system of claim 1, wherein the facial shield is disposed inside a frame that is coupled to the facial adapter.

11. The system of claim 1, wherein the facial shield comprises one or more materials selected from the group consisting of: polymethylmethacrylate (PMMA), polystyrene (PS), general purpose polystyrene (GPPS), styrene acrylonitrile (SAN), styrene methyl methacrylate (SMMA), polycarbonate (PC), high heat polycarbonate (HH-PC), polyethylene terephthalate (PET), polyethylene terephthalate glycol (PET-G), cellulose acetate butyrate (CAB), methyl methacrylate butadiene styrene (MBS), methyl methacrylate acrylonitrile butadiene styrene (MABS), styrene ethylene butylene styrene (SEBS), styrene butadiene copolymer (SB), polyetherimide (PE), polyethersulfone (PES), polysulfone (PSU), cycloolefin copolymer (COC), polylactic acid (PLA), and glass.

12. The system of claim 1, wherein the facial adapter is configured to compressively couple to the first portion of the face.

13. The system of claim 1, wherein the facial adapter is integrally coupled to the facial shield.

14. The system of claim 1, wherein the facial adapter is detachably coupled to the facial shield.

15. The system of claim 1, further comprising a frame configured to couple the facial adapter to the facial shield.

16. The system of claim 1, further comprising a filter coupled to the suction port.

17. The system of claim 1, wherein the access port comprises a cuttable material.

18. The system of claim 1, wherein the facial adapter or the facial shield comprises one or more grooves sized to accommodate one or more members selected from the group consisting of: an endotracheal tube, a temperature probe, and an orogastric tube.

19. The system of claim 1, wherein the procedure comprises one or more members selected from the group consisting of: a surgical procedure, a nasal surgical procedure, an oral surgical procedure, a maxillofacial surgical procedure, a dental procedure, an orthodontic procedure, an optometric procedure, and an ophthalmological procedure.

* * * * *